United States Patent [19]

Brandes et al.

[11] Patent Number: 4,831,048
[45] Date of Patent: May 16, 1989

[54] FUNGICIDAL ACTIVE COMPOUND COMBINATIONS

[75] Inventors: Wilhelm Brandes, Leichlingen; Helmut Kaspers; Hans Scheinpflug, both of Leverkusen; Graham Holmwood, Wuppertal, all of Fed. Rep. of Germany

[73] Assignee: Bayer Aktiengesellschaft, Leverkusen, Fed. Rep. of Germany

[21] Appl. No.: 141,876

[22] Filed: Jan. 6, 1988

[30] Foreign Application Priority Data

Jan. 15, 1987 [DE] Fed. Rep. of Germany ....... 3700923

[51] Int. Cl.$^4$ ..................... A01N 41/02; A01N 43/64
[52] U.S. Cl. ..................................... 514/383; 514/600
[58] Field of Search ................................ 514/383, 600

[56] References Cited

U.S. PATENT DOCUMENTS

| | | | |
|---|---|---|---|
| 4,532,341 | 7/1985 | Holmwood | 549/557 |
| 4,570,622 | 2/1986 | Bonnin et al. | 128/90 |
| 4,623,653 | 11/1986 | Brandes et al. | 514/383 |

FOREIGN PATENT DOCUMENTS

| | | |
|---|---|---|
| 135854 | 4/1985 | European Pat. Off. . |
| 0136021 | 4/1985 | European Pat. Off. . |
| 807406 | 1/1959 | United Kingdom . |

OTHER PUBLICATIONS

Plant Protection and Combating of Pests–p. 141, George Thieme Verlag, Stuttgart, 1977.

*Primary Examiner*—Allen J. Robinson
*Attorney, Agent, or Firm*—Sprung Horn Kramer & Woods

[57] ABSTRACT

A fungicidal composition comprising a fungicidally effective amount of (a) 1-(4-chlorophenyl)-4,4-dimethyl-3-(1,2,4-triazol-1-yl-methyl)-pentan-3-ol of the formula

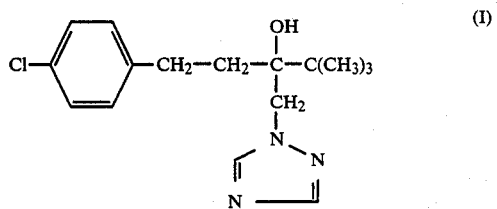

and (b) N,N-dimethyl-N'-(fluorodichloromethylmercapto)-N'-(4-methyl-phenyl)-sulphamide of the formula

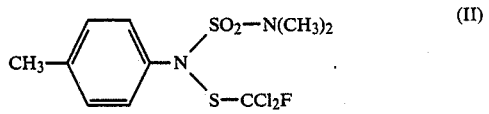

2 Claims, No Drawings

FUNGICIDAL ACTIVE COMPOUND COMBINATIONS

The present application relates to new active compound combinations which comprise, on the one hand, known 1-(4-chlorophenyl)-4,4-dimethyl-3-(1,2,4-triazol-1-yl-methyl)-pentan-3-ol, and, on the other hand, certain known fungicides, and which are very highly suitable for combating fungi.

It has already been disclosed that 1-(4-chlorophenyl)-4,4-dimethyl-3-(1,2,4-triazol-1-yl-methyl)-pentan-3-ol has a fungicidal potency (cf. EP-OS (European Published Specifications) No. 0,040,345). The activity of this substance is good; however, in many cases it leaves something to be desired at low application rates.

It is furthermore already known that N,N-dimethyl-N'-(fluorodichloromethylmercapto)-N'-(4-methyl-phenyl)-sulphamide can be employed for combating fungi (cf. K. H. Büchel "Pflanzenschutz und Schädlingsbekämpfung" [Plant Protection and Combating of Pests], page 141, Georg Thieme Verlag, Stuttgart, 1977). However, the action of this substance is likewise not always satisfactory at low application rates.

It has now been found that the new active compound combinations made of (a) 1-(4-chlorophenyl)-4,4-dimethyl-3-(1,2,4-triazol-1-yl-methyl)-pentan-3-ol of the formula

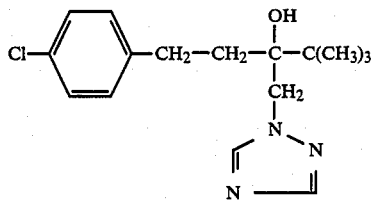

and (b) N,N-dimethyl-N'-(fluorodichloromethylmercapto)-N'-(4-methyl-phenyl)-sulphamide of the formula

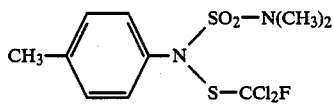

have very good fungicidal properties.

Surprisingly, the fungicidal action of the active compound combinations according to the invention is significantly greater than the sum of the actions of the individual active compounds. An unforeseeable, true synergistic effect is therefore present, and not only a summation of actions.

The active compounds contained in the active compound combinations according to the invention have already been disclosed (cf. EP-OS (European Published Specification) No. 0,040,345 und K. H. Büchel "Pflanzenschutz and Schädlingsbekämpfung" [Plant Protection and Combating of Pests] page 141, Georg Thieme Verlag, Stuttgart 1977).

When the active compounds are present in the active compound combinations according to the invention in certain weight ratios, synergistic effect becomes particularly apparent. However, the weight ratios of the active compounds in the active compound combinations can be varied in a relatively wide range. In general, 0.1 to 100 parts by weight, preferably 1 to 20 parts by weight, of active compound of the formula (II) are present per part by weight of active compound of the formula (I).

The active compound combinations according to the invention have very good fungicidal properties and can be employed for combating phytopathogenic fungi, such as Plasmodiophoromycetes, Oomycetes, Chytridiomycetes, Zygomycetes, Ascomycetes, Basidiomycetes and Deuteromycetes etc.

The active compound combinations according to the invention are particularly highly suitable for combating Botrytis species in viticulture, in soft fruit and in vegetable growing, furthermore for combating Monilia species in drupe growing and for combating Sclerotinia species in various crops, such as, for example, rape.

The good toleration, by plants, of the active compound combinations at the concentrations required for combating plant diseases permits treatment of aboveground parts of plants, vegetative propagation stock and seeds, and of the soil.

The active compound combinations according to the invention can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compound with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl napthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, aryl-sulphonates as well as albumen hydrolysis products. As dispersing agents there are suitable: for example Ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound combinations according to the invention can be present in the formulations as a mixture with other known active compounds, such as fungicides, insecticides, acaricides and herbicides, as well as in mixtures with fertilizers.

The active compound combinations can be used as such or in the form of their formulations or the use forms prepared therefrom, such as ready-to-use solutions, emulsifiable concentrates, emulsions, suspensions, wettable powders, soluble powders, and granules. They are used in the customary manner, for example by watering, spraying, atomizing, scattering, brushing on, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The good fungicidal action of the active compound combinations according to the invention can be seen from the following examples. Whereas the individual active compounds have weaknesses in the fungicidal action, the combinations exhibit an action which extends beyond a simple summation of actions.

A synergistic effect in fungicides is always present when the fungicidal action of the active compound combinations is greater than the sum of the actions of the individual applied active compounds.

The action to be expected for a given combination of two active compounds can be calculated as follows (cf. Colby, S. R., "Calculating synergistic and antagonistic responses of herbicide combinations", Weeds 15, pages 20–22, 1967):
when
X denotes the disease infestation, expressed in % of the untreated control, when active compound A is used in a concentration of m ppm,
Y denotes the disease infestation, expressed in % of the untreated control, when active compound B is used in a concentration of n ppm, and
E denotes the disease infestation expected, expressed in % of the untreated control, when active compounds A and B are used in concentration of m and n ppm,
then $$E = (X \times Y)/100$$

If the actual fungicidal action is greater than calculated, the combination is superadditive in its action, i.e. a synergistic effect is present. In this case, the infestation actually observed must be less than the value calculated from the formula above for the expected infestation (E).

From the table of the following example, it can clearly be seen that the action found for the active compound combinations according to the invention is greater than the calculated value, i.e. a synergistic effect is present.

EXAMPLE A

Botrytis test (bean)/protective

To produce a suitable preparation of active compound, sprayable, commercially available active compound formulation is in each case diluted with water to the desired concentration.

To test for protective activity, young plants are sprayed with the appropriate preparation of active compound (individual active components or combinations thereof) until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

The active compounds, the active compound concentrations and the experimental results can be seen from the following table.

TABLE A

| | Botrytis test (bean)/protective | | |
|---|---|---|---|
| Active compounds | Active compound concentration in the spray liquor in ppm | Disease infestation in % of the untreated control | |
| — (control) | — | = 100 | |
| (I) | 5 | 71 | |
| | 2,5 | 80 | |
| (II) | 20 | 74 | |
| | 10 | 88 | |
| | | found | calculated* |
| (I) + (II) | 5 + 20 | 18 | 53 |
| (I) + (II) | 2.5 + 10 | 37 | 70 |

*Calculated from the formula $E = \frac{X \times Y}{100}$.

It will be understood that the specification and examples are illustrative but not limitative of the present invention and that other embodiments within the spirit and scope of the invention will suggest themselves to those skilled in the art.

What we claim is:

1. A fungicidal composition comprising a fungicidally effective amount of
   (a) 1-(4-chlorophenyl)-4,4-dimethyl-3-(1,2,4-triazol-1-yl-methyl)-pentan-3-ol of the formula

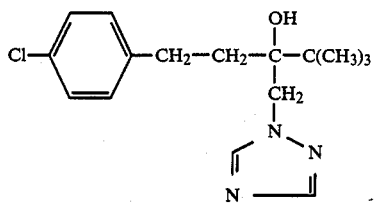 (I)
and
(b) N,N-dimethyl-N'-(fluorodichloromethylmercapto)-N'-(4-methyl-phenyl)-sulphamide of the formula
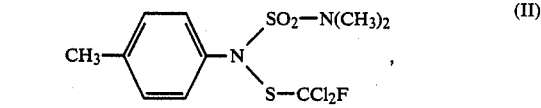 (II)
the weight ratio of (I):(II) being about 1:4.
2. A method of combating fungi which comprises applying thereto or to a fungus habitat a fungicidally effective amount of a composition according to claim 1.
* * * * *